(12) United States Patent
Hirabuki et al.

(10) Patent No.: US 9,579,447 B2
(45) Date of Patent: Feb. 28, 2017

(54) BLOOD BAG SYSTEM AND BLOOD TREATMENT METHOD

(71) Applicant: TERUMO KABUSHIKI KAISHA, Tokyo (JP)

(72) Inventors: Makoto Hirabuki, Leuven (BE); Masayoshi Higashi, Bangkok (TH)

(73) Assignee: TERUMO KABUSHIKI KAISHA, Shibuya-ku, Tokyo (JP)

( * ) Notice: Subject to any disclaimer, the term of this patent is extended or adjusted under 35 U.S.C. 154(b) by 0 days.

(21) Appl. No.: 14/846,164

(22) Filed: Sep. 4, 2015

(65) Prior Publication Data

US 2015/0374899 A1     Dec. 31, 2015

Related U.S. Application Data

(60) Division of application No. 13/467,813, filed on May 9, 2012, now abandoned, which is a continuation of
(Continued)

(30) Foreign Application Priority Data

Nov. 10, 2009 (JP) .................................. 2009-257118

(51) Int. Cl.
  *A61B 19/00* (2006.01)
  *A61M 1/36* (2006.01)
  *A61M 1/02* (2006.01)

(52) U.S. Cl.
  CPC ........ *A61M 1/3693* (2013.01); *A61M 1/0218* (2014.02); *A61M 1/0236* (2014.02); *A61M 1/029* (2013.01)

(58) Field of Classification Search
  CPC .... A61M 1/3693; A61M 1/3639; A61M 1/30; A61M 1/16; A61M 1/3679; A61M 1/3633; A61M 1/34; A61M 1/3627
  (Continued)

(56) References Cited

U.S. PATENT DOCUMENTS 4,767,541 A  *  8/1988  Wisdom .............. A61M 1/0209
                                                210/749
5,071,570 A     12/1991  Shiraki et al.
(Continued)

FOREIGN PATENT DOCUMENTS

DE          4340678 A1    6/1995
DE         19949109 A1    4/2001
(Continued)

OTHER PUBLICATIONS

International Search Report (PCT/ISA/210) issued on Jan. 11, 2011, by the Japanese Patent Office as the International Searching Authority for International Application No. PCT/JP2010/068808.

*Primary Examiner* — Philip R Wiest
(74) *Attorney, Agent, or Firm* — Buchanan Ingersoll & Rooney PC

(57) ABSTRACT

A blood bag system includes: a first bag in which blood containing multiple components is stored; a second bag in which a relative medium-density component is stored; a third bag in which a relative low-density component is stored; a first tube through which the relative low-density component and the relative medium-density component are transported from the first bag to the second bag; and a second tube through which the relative low-density component is transported from the first bag to the third bag. A blood treatment method involves: centrifuging blood containing multiple components in a first bag, transporting a low-density component from the first bag to a third bag through a first tube and transporting a relative medium-density component from the first bag to the second bag through the first tube.

8 Claims, 8 Drawing Sheets

Related U.S. Application Data application No. PCT/JP2010/068808, filed on Oct. 25, 2010.

(58) Field of Classification Search
USPC .................................................. 604/6.01–6.06
See application file for complete search history.

(56) References Cited

U.S. PATENT DOCUMENTS

| | | | |
|---|---|---|---|
| 5,102,407 A | 4/1992 | Carmen et al. | |
| 5,167,656 A | 12/1992 | Lynn | |
| 5,494,592 A | 2/1996 | Latham, Jr. et al. | |
| 5,523,004 A | 6/1996 | Tanokura et al. | |
| 5,651,766 A | 7/1997 | Kingsley et al. | |
| 5,836,934 A | 11/1998 | Beshel | |
| 6,296,602 B1 | 10/2001 | Headley | |
| 6,364,864 B1 | 4/2002 | Mohiuddin et al. | |
| 6,495,039 B1 | 12/2002 | Lee et al. | |
| 6,910,998 B2 | 6/2005 | Eberle | |
| 2001/0037078 A1 | 11/2001 | Lynn et al. | |
| 2002/0011452 A1 | 1/2002 | Mari et al. | |
| 2003/0176267 A1 | 9/2003 | Eberle | |
| 2003/0195104 A1* | 10/2003 | Hlavinka | A61M 1/0209 494/21 |
| 2004/0097862 A1 | 5/2004 | Lampeter et al. | |
| 2007/0179423 A1 | 8/2007 | Felt et al. | |
| 2008/0135462 A1 | 6/2008 | Park et al. | |
| 2009/0286221 A1 | 11/2009 | Klip et al. | |
| 2010/0152013 A1 | 6/2010 | Eberle et al. | |
| 2010/0170858 A1 | 7/2010 | Eberle et al. | |

FOREIGN PATENT DOCUMENTS

| | | |
|---|---|---|
| JP | 62-258322 A | 11/1987 |
| JP | 7-136243 A | 5/1995 |
| JP | 9-000603 A | 1/1997 |
| JP | 10-504224 A | 4/1998 |
| JP | 10-279489 A | 10/1998 |
| JP | 2001-198212 A | 7/2001 |
| JP | 2001-259022 A | 9/2001 |
| JP | 2003-501153 A | 1/2003 |
| JP | 2005-066018 A | 3/2005 |
| JP | 2005-508707 A | 4/2005 |
| JP | 2006-212439 A | 8/2006 |
| JP | 2008-145420 A | 6/2008 |
| JP | 2008-220969 A | 9/2008 |
| JP | 2009-525153 A | 7/2009 |
| WO | WO 2008/002135 A1 | 1/2008 |
| WO | WO 2008/148808 A1 | 12/2008 |
| WO | WO 2008/148811 A1 | 12/2008 |

* cited by examiner

BLOOD BAG SYSTEM AND BLOOD TREATMENT METHOD

CROSS REFERENCES TO RELATED APPLICATIONS

This application is a divisional of U.S. application Ser. No. 13/467,813 filed on May 9, 2012, which is a continuation of International Application No. PCT/JP2010/068808 filed on Oct. 25, 2010, and claims priority to Japanese Application No. 2009-257118 filed on Nov. 10, 2009, the entire content of all three of which is incorporated herein by reference.

TECHNICAL FIELD

The present invention generally relates to a blood bag system and a blood treatment method for centrifuging whole blood and storing individual blood components in respective bags.

BACKGROUND DISCUSSION

Conventionally, whole blood transfusion in which all the components of blood obtained by blood donation are put to transfusion has been common practice. With the recent progress of technology, blood component transfusion has come to be carried out in which the blood obtained is separated into its components such as red blood cells, platelets and plasma and only the component(s) necessary for a patient is transfused into the patient. Using blood component transfusion, the burden on the patient's circulatory system and side effects can be alleviated, and generally effective utilization of donated blood can be achieved.

The blood (whole blood) obtained by blood donation is centrifuged to be thereby separated into a light supernatant PPP (platelet poor plasma) fraction, a heavy precipitated CRC (concentrated red cell) fraction, and buffy coat therebetween. The buffy coat contains leukocytes, platelets and red cells; especially, as for platelets, the proportion of young fresh platelets is high.

In order to separate whole blood into the three blood components including platelet poor plasma, concentrated red cells and buffy coat, and further to transport the blood components into predetermined storage bags, there has hitherto been used a blood bag system configured by connecting a plurality of bags using a plurality of tubes. An example is disclosed in U.S. Pat. No. 6,910,998.

One conventional example of a blood bag system includes a first bag (combined buffy coat bag and whole blood bag) for storing whole blood, a first tube connected at its one end to an upper portion of the first bag, a second bag (plasma bag) which is connected to the other end of the first tube and in which platelet poor plasma is to be stored, a second tube connected at its one end to a lower portion of the first tube, and a third bag (red cell bag) which is connected to the other end of the second tube and in which concentrated red cells are to be stored. In order to preserve whole blood in the state of being separated into the blood components by use of the blood bag system configured as just-mentioned, the whole blood in the first bag is centrifuged to be separated into platelet poor plasma, concentrated red cells and buffy coat, and, thereafter, the platelet poor plasma is transported to the second bag through the first tube connected to an upper portion of the first bag, and the concentrated red cells are transported to the third bag through the second tube connected to a lower portion of the first bag.

The specification of U.S. Pat. No. 6,910,998 discloses a blood bag system similar to the one conventional example mentioned above.

A centrifuging and transporting apparatus which permits a step of centrifuging whole blood and a step of transporting blood components obtained by centrifugation to be performed by a single apparatus may be configured to include a centrifugal drum having a plurality of unit insertion holes and driven to rotate in a circumferential direction and a plurality of insert units to be inserted in the unit insertion holes. An example is disclosed in U.S. Pat. No. 6,910,998. In this case, the insert unit permits the above-mentioned blood bag system to be mounted thereto.

When the above-mentioned blood bag system is supposed to be mounted to the centrifuging and transporting apparatus configured as above, difficulties can arise. A first bag in the above-mentioned blood bag system has a top-and-bottom (TAB) type bag structure in which a first tube is connected to an upper portion thereof and a second tube is connected to a lower portion thereof. Therefore, in mounting the first tube to the above-mentioned insert unit, the second tube provided at the lower portion of the first bag must be laid around upward from the lower side (bottom side) of the insert unit, and the handling operation is bothersome, so that it is difficult to smoothly carry out the mounting operation. In addition, if the second tube undergoes kinking (torsion or sharp bending) due to the handling of the second tube, the second tube may be closed, possibly making it impossible to transport blood components.

SUMMARY

The blood bag system includes: a first bag in which blood containing a plurality of components is stored; a second bag in which a relative medium-density component obtained by centrifugation of the blood in the first bag is stored; a third bag in which a relative low-density component obtained by centrifugation of the blood in the first bag is stored; a first tube through which an upper portion of the first bag and an inlet of the second bag are connected and through which the relative low-density component and the relative medium-density component are transported from the first bag to the second bag; and a second tube through which an outlet of the second bag and the third bag are connected and through which the relative low-density component is transported from the first bag to the third bag by way of the first tube and the second bag.

The blood bag system is configured so that blood containing a plurality of components and contained in the first bag is separated into three layers including a relative low-density component, a relative medium-density component and a relative high-density component, by applying a centrifugal force to the blood, and the first bag is pressed so that the relative low-density component is transported from the first bag to the third bag through the first tube, the second bag and the second tube, whereas the relative medium-density component is transported from the first bag to the second bag through the first tube. Of the blood components centrifugally separated, the relative medium-density component is stored in the second bag, whereas the relative low-density component is stored in the third bag, and the remaining relative high-density component is stored in the first bag. Consequently, the blood can be separated into the relative low-density component, relative the medium-density component and the relative high-density components, and these components can be preserved in the respective bags. The first tube through which the relative medium-density component and the relative low-density component are transported from the first bag to the second bag and the third bag is connected to the upper portion of the first bag, so that a tube to be connected to a lower portion of the first bag is unnecessary (i.e., there are no tubes connected to the lower portion of the first bag), and tubes are connected only to the upper portion of the first bag in this configuration. Accordingly, the bag configuration is simplified so that convenience for the user to use a blood bag system is enhanced. In addition, since handling of tubes in mounting the blood bag system to a centrifuging and transporting apparatus is facilitated, the mounting of the system to the centrifuging and transporting apparatus becomes easy to carry out. Since the second bag is used only for storage of the relative medium-density component and its capacity may be set according to the amount of the relative medium-density component to be stored therein, the second bag can be reduced in size, as compared with a relative medium-density component bag according to the related art. Consequently, in the case where the relative medium-density component is buffy coat, it is possible to reduce the amount of buffy coat left in the second bag, and to enhance platelet recovery late, at the time of preparing a platelet preparation by buffy coat pooling conducted as a subsequent step.

The second bag can be configured such that the cross-sectional area of a channel at the outlet is smaller than the cross-sectional area of a channel at the inlet. The rate of flow into the third bag is thus suppressed, whereby the medium-density component can be inhibited or prevented from flowing into the third bag.

The blood bag system can also include a first clamp by which the first tube is closed and opened; and a second clamp by which the second tube is closed and opened. With this arrangement, upon detecting the transfer of a predetermined component into the first tube at the time of transporting the relative low-density component and the relative medium-density component from the first bag to the second bag, the second clamp is operated to close the second tube, whereby the predetermined component is prevented from flowing into the third bag. In addition, with the first tube closed by operating the first clamp when the first bag has been pressed by a predetermined amount, it is possible to collect a predetermined amount of a blood component into the second bag and to prevent the relative high-density component from flowing into the second bag.

The blood bag system can also include a fourth bag configured to store a relative high-density component transported from the first bag. The system can also include a filter disposed between the first bag and the fourth bag and by which predetermined cells are removed, a third tube through which an upper portion of the first bag and an inlet of the filter are connected and through which the relative high-density component is transported from the first bag to the filter, and a fourth tube through which an outlet of the filter and the fourth bag are connected and through which the relative high-density component is transported from the filter to the fourth bag. It is thus possible to filter the relative high-density component left in the first bag by the filter to thereby remove predetermined cells and to store in the fourth bag the relative high-density component freed of the predetermined cells. In addition, since the third tube interconnects the first bag and the filter is connected to the upper portion of the first bag, a tube connected to a lower portion of the first bag is unnecessary, and tubes are connected only to the upper portion of the first bag in this configuration. Accordingly, even in the configuration in which the filter is provided, it is relatively easy to lay around the tubes in mounting the blood bag system to a centrifuging and transporting apparatus and, hence, it is rather easy to mount the blood bag system to the centrifuging and transporting apparatus.

The blood containing the plurality of components is preferably whole blood, and the relative low-density component, the relative medium-density component and the relative high-density component are plasma, buffy coat and concentrated red cells, respectively.

Another aspect of the disclosure here involves a blood treatment method comprising centrifuging blood containing a plurality of components into a relative low-density component, relative a medium-density component and a relative high-density component in a first bag, and transporting the relative low-density component from the first bag to a third bag through a first tube connected to an upper portion of the first bag and transporting the relative medium-density component from the first bag to a second bag provided between the first bag and the third bag through the first tube, by pressing the first bag.

The pressing of the first bag is performed to cause the relative low-density component and the relative medium-density component to flow out from the first bag through the first tube in the order of the relative low-density component and the relative medium-density component, wherein the relative low-density component is transported from the first bag to the third bag through the second bag and a second tube connected to an outlet of the second bag, and the relative medium-density component is transported to the second bag through the first tube.

The relative medium-density component is stored in the second bag, whereas the relative low-density component is stored in the third bag, and the remaining relative high-density component is stored in the first bag. The tubes are connected only to the upper portion of the first bag and so the convenience in use of the blood bag system is enhanced through simplification of the bag configuration, and handling of the tubes at the time of mounting the blood bag system to a centrifuging and transporting apparatus is facilitated, whereby the mounting of the system to the centrifuging and transporting apparatus is facilitated. Also, the second bag can be reduced in size, as compared with a relative medium-density component bag according to the related art. In the case where the relative medium-density component is buffy coat, therefore, the amount of the buffy coat left in the second bag at the time of preparing a platelet preparation by buffy coat pooling can be reduced, and platelet recovery rate can be enhanced.

While transporting the relative low-density component and the relative medium-density component from the first bag to the second bag, the kind of a solution flowing through the first tube is detected, and a channel in the second tube is closed upon detection of transfer of the relative medium-density component into the first tube. The relative medium-density component is thus prevented from flowing into the third bag.

During the separation or transporting, a channel in the first tube is closed when the first bag has been pressed by a predetermined amount. It is thus possible to collect a predetermined amount of a blood component into the second bag and to inhibit or prevent the relative high-density component from flowing into the second bag.

The blood treatment method also includes transporting, after the separation step, the relative high-density component left in the first bag from the first bag to a filter by which predetermined cells are removed, through a third tube connected to an upper portion of the first bag, and transporting the relative high-density component passed through the filter from the filter to a fourth bag. Because the third tube is connected to the upper portion of the first bag, a tube connected to a lower portion of the first bag is unnecessary, and tubes are connected only to the upper portion of the first bag in this configuration. Accordingly, even in the configuration wherein the filter is provided, it is rather easy to lay around the tubes at the time of mounting to a blood bag system for use in the blood treatment method to a centrifuging and transporting apparatus, and it is also relatively easy to mount the blood bag system to the centrifuging and transporting apparatus.

The blood with which the method is performed is whole blood, and the relative low-density component, the relative medium-density component and the relative high-density component are plasma, buffy coat and concentrated red cells, respectively.

Another aspect of the disclosure involves a blood bag system comprising: a first bag possessing an interior surrounded configured to store blood containing a plurality of components including a relative medium-density component and a relative low-density component, with the first bag possessing a top wall, an oppositely disposed bottom wall, and two oppositely positioned side walls each extending between the top wall and the bottom wall, the top wall of the first bag including a through opening which opens to the interior of the first bag; a second bag possessing an interior configured to store the relative medium-density component obtained by centrifugation of the blood in the first bag, with the second bag including an inlet in fluid communication with the interior of the second bag and an outlet in fluid communication with the interior of the second bag; and a third bag possessing an interior configured to store the relative low-density component obtained by centrifugation of the blood in the first bag. A first tube possesses a first end connected to the top wall of the first bag so that the first tube is fluidly communicatable with the interior of the first bag by way of the through opening in the top wall of the first bag and possesses a second end connected to the inlet of the second bag to permit the relative low-density component and the relative medium-density component in the interior of the first bag to be transported to the interior of the second bag. A second tube possesses a first end connected to the outlet of the second bag and a second end connected to the third bag to permit the relative low-density component in the interior of the first bag to be transported to the interior of the third bag by way of the first tube and the second bag.

DETAILED DESCRIPTION

A blood bag system 10 and a blood treatment method will be described below by reference to embodiments disclosed as examples and while referring to the accompanying drawings.

Figure 1:
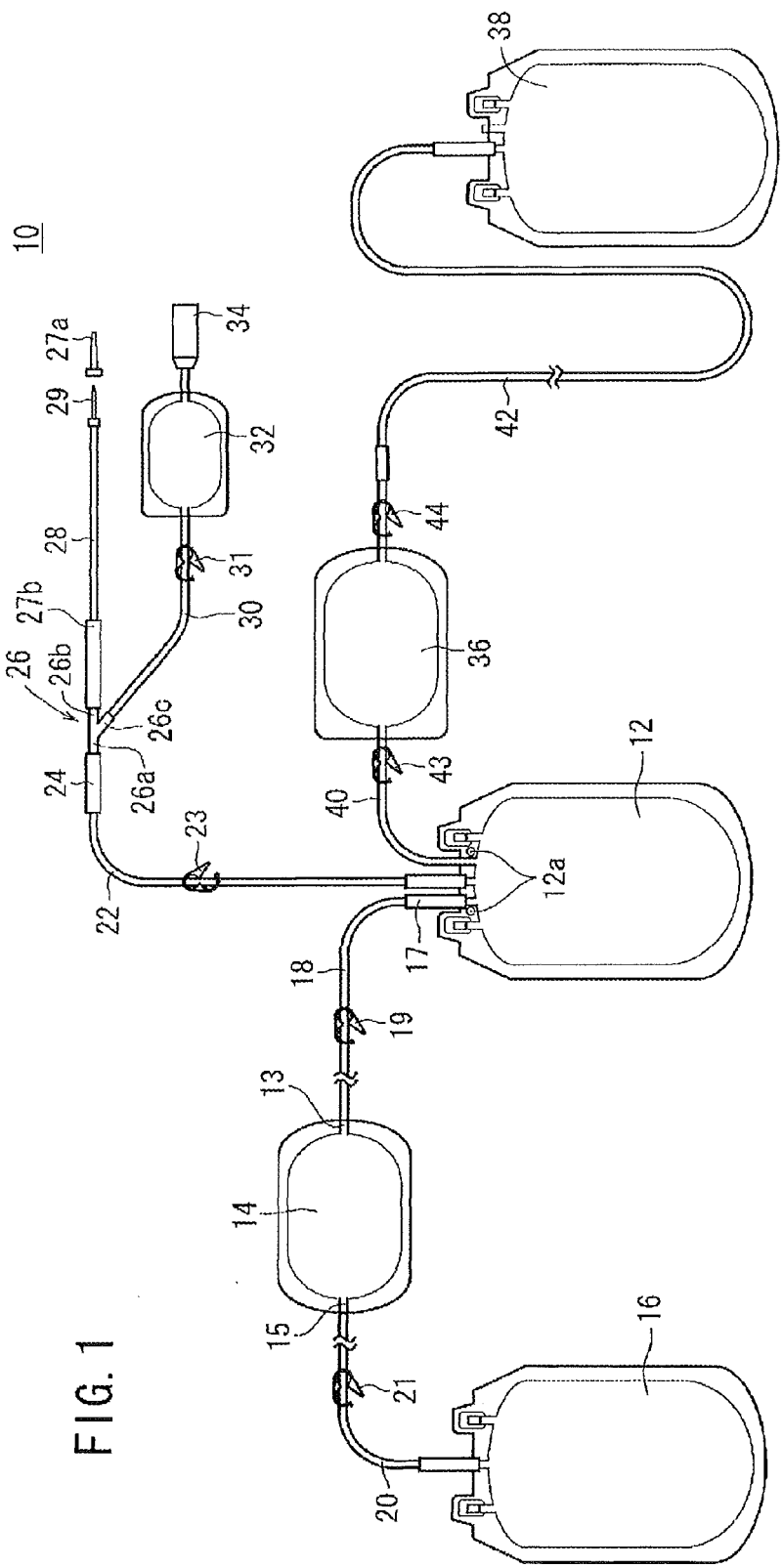
FIG. 1 is a plan view of a blood bag system according to one embodiment disclosed here by way of example.

The blood bag system 10 illustrated in FIG. 1 is for centrifuging whole blood containing a plurality of components into three components, namely a low-density component (relative low-density component), a medium-density component (relative medium-density component) and a high-density component (relative high-density component) (in this embodiment, whole blood is centrifuged into three components including plasma, buffy coat and concentrated red cells), and containing and preserving the components separately in different bags.

As shown in FIG. 1, the blood bag system 10 includes: a first bag 12 in which blood containing a plurality of components is contained; a second bag 14 in which a medium-density component obtained by centrifuging the blood in the first bag 12 is stored; a third bag 16 in which a low-density component obtained by centrifuging the blood in the first bag 12 is contained; a first tube 18 through which an upper portion of the first bag 12 and an inlet 13 of the second bag 14 are connected and through which the low-density component and the medium-density component are transported from the first bag 12 to the second bag 14; and a second tube 20 by which an outlet 15 of the second bag 14 and the third bag 16 are connected and through which the low-density component is transported from the first bag 12 to the third bag 16 by way of the first tube 18 and the second bag 14.

The first bag 12, the second bag 14 and the third bag 16 are each fabricated by a method in which flexible sheet materials made of a flexible resin such as polyvinyl chloride and polyolefin are placed on each other and are fused (by heat fusing or high-frequency fusing) or adhered to each other at peripheral sheet portions into a bag form. A first flow blood bag 32 and a red cell bag 38 which will be described later are also configured in a bag form.

In the illustrated embodiment disclosed as an example, the bags 12, 16, 38 are configured to include two oppositely positioned sides each extending between the top and the bottom of the bag. The tube 18 intersects the top of the bag 12, 16, 38 and the lumen of the tube is thus communicatable with the interior of the first bag 12. Similarly, the tube 20 intersects the top of the third bag 16 and the lumen in the tube 20 is thus in fluid communication with the interior of the third bag 16. The same is also true with respect to the tube connected to the top of the red cell bag 38.

The first bag 12 is a bag for containing (storing) blood (whole blood) collected from a donor. Hereafter, the first bag 12 will be referred to as the "blood collection bag." The blood collection bag 12 is configured to contain the whole blood at the time of blood collection. After the whole blood is centrifuged and buffy coat is transported to the second bag 14 while the plasma is transported to the third bag 16 as will be described later, the blood collection bag 12 is used for containing and preserving the unfiltered concentrated red cells which are the remaining component. In other words, the blood collection bag 12 serves both as a whole blood containing bag and as an unfiltered concentrated red cell containing bag.

Preferably, an anticoagulant is preliminarily contained in the blood collection bag 12. The anticoagulant is normally a solution, and examples thereof include ACD-A solution, CPD solution, CPDA-1 solution, and heparin sodium solution. The proper amount of anticoagulant is prepared corresponding to the amount of blood to be collected.

One end of a blood collection tube (proximal-side blood collection tube) 22 is connected to an upper portion of the blood collection bag 12. A clamp 23 by which a lumen in the blood collection tube 22 is closed and opened is provided at an intermediate portion of the blood collection tube 22. One end of a sealing member (breaking communication member) 24 is connected to the other end of the blood collection tube 22. The sealing member 24 is so configured as to close the channel in an initial condition and to open the channel by a breaking operation.

Such a sealing member 24 as this includes a tube formed, for example, from a flexible resin such as vinyl chloride, and a tubular body which is connected to the inside of the tube in a liquid-tight manner, is closed at one end thereof and has a brittle part at a portion in the longitudinal direction thereof. To put the sealing member 24 into an open (communicating) state, the tubular body is bent from the outside of the tube by fingers or the like to thereby break the brittle part. Consequently, a channel in the tube which has been closed by the tubular body is opened, whereby the sealing member 24 is put into an open state.

To the other end of the sealing member 24 is connected a first port 26a of a branch connector 26. To a second port 26b of the branch connector 26 is connected one end of a blood collection tube (distal-side blood collection tube) 28, and to the other end of the blood collection tube 28 is connected a blood collection needle 29. Before use, a cap 27a is mounted in covering relation to the blood collection needle 29, and, after use, a needle guard 27b is mounted to the blood collection needle 29. The needle guard 27b is so disposed as to be movable along the longitudinal direction of the blood collection tube 28.

To a third port 26c of the branch connector 26 is connected one end of a branch tube 30. At an intermediate portion of the branch tube 30 is provided a clamp 31 by which a channel in the branch tube 30 is closed and opened. To the other end of the branch tube 30 is connected a first flow blood bag 32. At the time of collecting blood from a donor, a first flow (collected blood first flow) of the blood collected is first contained into the first flow blood bag 32 in a predetermined amount, before containing the blood into the blood collection bag 12. In this case, while the sealing member 24 is kept in a closed state (initial state), the clamp 31 is put into an open state, whereby the collected blood first flow is inhibited from flowing to the blood collection tube 22 side, namely, to the blood collection bag 12 side. At the same time, the collected blood first flow can be led into the first flow blood bag 32 through the blood collection tube 28, the branch connector 26 and the branch tube 30.

A sampling port 34 is connected to the first flow blood bag 32, and, by attaching a blood collection tube to the sampling port 34, the collected blood first flow is sampled into the blood collection tube. The collected blood first flow thus sampled serves as blood for testing. Depending on the use, the part ranging from the branch connector 26 to the sampling port 34 may be omitted.

The second bag 14 is a bag to contain (store) buffy coat (BC). Hereafter, the second bag 14 will be referred to as the "BC bag." The BC bag 14 has a bag structure of a top-and-bottom (TAB) form wherein the inlet 13 is provided at one end and the outlet 15 is provided at the other end. The BC bag 14 is so set as to have a necessary and sufficient capacity, taking into account the amount of buffy coat to be collected; though the capacity is smaller than the capacity of the blood collection bag 12.

The third bag 16 is a bag in which to contain (store) and preserve plasma. Hereafter, the third bag 16 will be referred to as the "plasma bag."

The first tube 18 is connected to an upper portion of the blood collection bag 12. In the present embodiment, a sealing member 17 is provided at that end portion of the first tube 18 which is located on the blood collection bag 12 side. The sealing member 17 has the same configuration and function as those of the above-mentioned sealing member 24. In addition, a first clamp 19 by which a channel in the first tube 18 is closed and opened is provided at an intermediate portion of the first tube 18.

The second tube 20 is connected at its one end to the outlet 15 of the BC bag 14, and is connected at its other end to the plasma bag 16. A second clamp 21 by which a channel in the second tube 20 is closed and opened is provided at an intermediate portion of the second tube 20.

As shown in FIG. 1, the blood bag system according to this embodiment further includes a fourth bag (hereafter referred to as the "red cell bag") 38 into which to contain (store) and preserve concentrated red cells transported from the blood collection bag 12, a filter 36 which is disposed between the blood collection bag 12 and the red cell bag 38 and by which predetermined cells are removed, a third tube 40 by which an upper portion of the blood collection bag 12 and an inlet of the filter 36 are connected, and a fourth tube 42 through which an outlet of the filter 36 and the red cell bag 38 are connected. In the present embodiment, the filter 36 is configured as a leukocyte removal filter.

A clamp 43 by which a channel in the third tube 40 is closed and opened is provided at an intermediate portion of the third tube 40. A clamp 44 by which a channel in the fourth tube 42 is closed and opened is provided at an intermediate portion of the fourth tube 42.

Each of the tubes (inclusive of the first tube 18 and the second tube 20) in the blood bag system 10 is a tube made of a transparent flexible resin and a lumen extending between opposite ends of the tube. Each of the clamps (inclusive of the first clamp 19 and the second clamp 21) may be a standard product that has been used conventionally. In addition, it is recommendable to preliminarily color the clamps separately in different colors according to the locations of use and the intended uses. At the time of sterilization and during stock before use of the blood bag system 10, each of the clamps is in an open state and the inside of each of the bags is in a communicating and uniform sterilized state.

Figure 2:
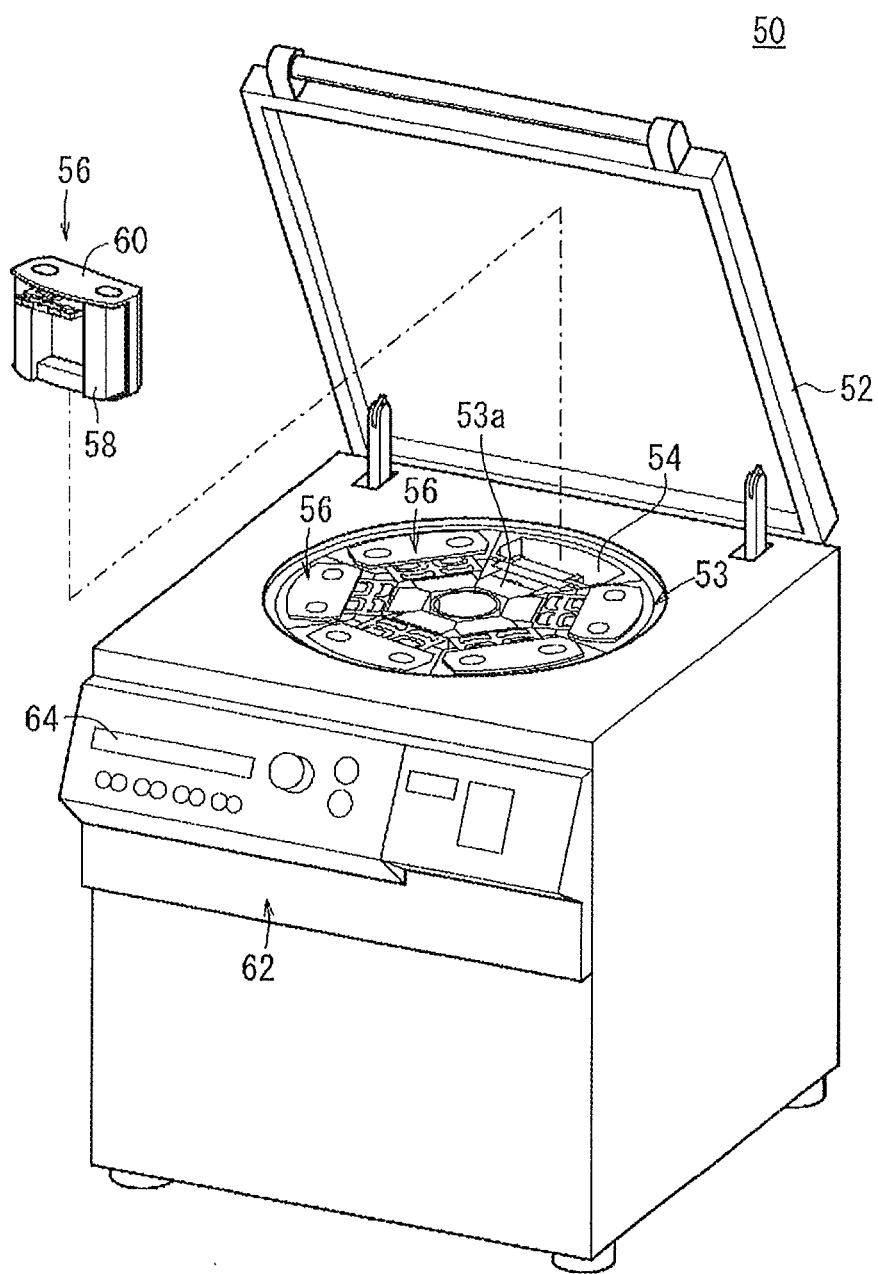
FIG. 2 is a perspective view of a centrifuging and transporting apparatus.

The blood bag system 10 according to the present embodiment can be used, for example, in the state of being mounted to a centrifuging and transporting apparatus (automatic centrifugal separator) 50 as shown in FIG. 2. This centrifuging and transporting apparatus 50 is used for dividing whole blood contained in the blood collection bag 12 into three layers (components) including plasma, buffy coat and concentrated red cells, transporting the buffy coat to the BC bag 14, while transporting the plasma to the plasma bag 16, and leaving the concentrated red cells in the blood collection bag 12.

For ease in understanding the method for using the blood bag system 10 disclosed here, the configuration of the centrifuging and transporting apparatus 50 will be described below. In the following description, the direction of arrows A will be referred to as the radial direction, and the direction of arrows B as the circumferential direction. The circumferential direction is strictly the direction along the circular arc as indicated by arrows B, but, for convenience of description, the direction orthogonal to arrows A at a location being described will also be referred to as the circumferential direction.

As shown in FIG. 2, the centrifuging and transporting apparatus 50 is box-shaped, and includes an openable/closable cover 52 at the top, a centrifugal drum (centrifuging means for centrifuging) 53 in the inside, six unit insertion holes 54 provided at regular angular (60°) intervals inside the centrifugal drum 53, six insert units 56 inserted in respective ones of the unit insertion holes, and six pushers (pressing means) 66 (see FIG. 3) which are provided at a central region and which can each be advanced and retracted in the rotational radial direction relative to each insert unit 56. The centrifuging and transporting apparatus 50 is operated based on operations on a console section 62 provided at the front surface thereof, is controlled by a microcomputer, and is configured to display predetermined information on a monitor 64.

Figure 3:
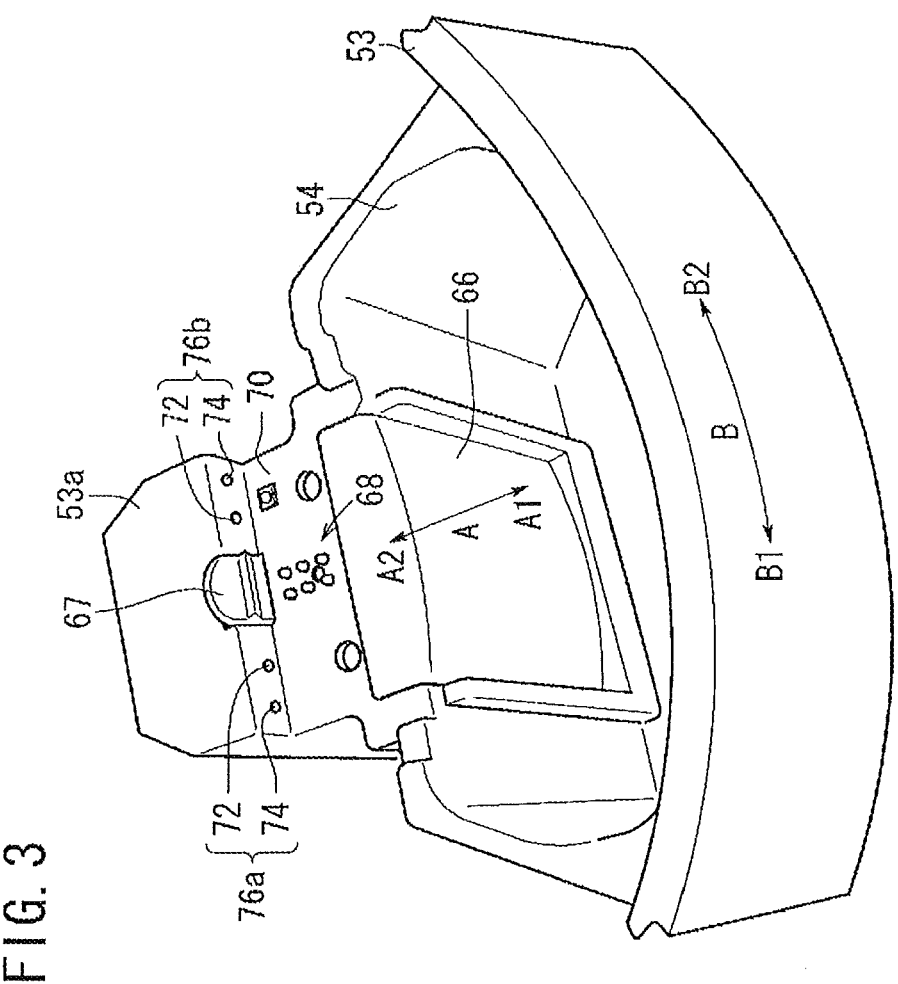
FIG. 3 is a partial enlarged perspective view of a centrifugal drum in the centrifuging and transporting apparatus.

As shown in FIG. 3, a central body 53a of the centrifugal drum 53 has a holding lever 67 biased by an elastic body to hold an end portion of a tube holder 80 (described later), electrodes 68, first rods 72 and second rods 74, and the pusher 66. The first rods 72 and the second rods 74, provided in two pairs, are driven to advance and retract in the radial direction A. The rods on the side of a first circumferential direction B1 constitute a first clamp driving means 76a for opening and closing the first clamp 19 (see FIG. 1), while the rods on the side of a second circumferential direction B2 constitute a second clamp driving means 76b for opening and closing the second clamp 21 (see FIG. 1). The part shown in FIG. 3 may be configured as a unit, and six such units may be combined in the circumferential direction.

Figure 4:
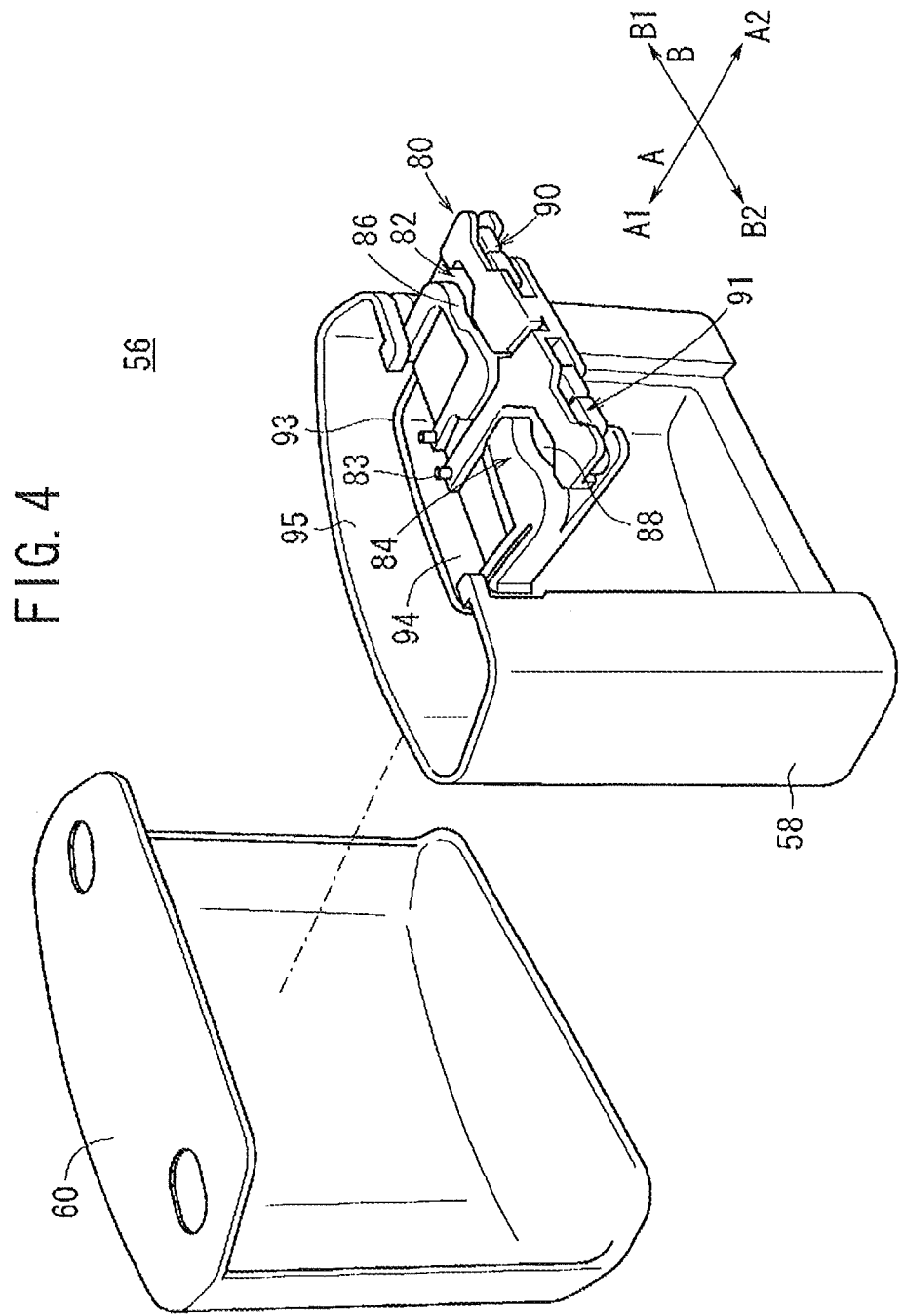
FIG. 4 is an exploded perspective view of an insert unit.

FIG. 4 is an exploded perspective view of the insert unit 56 as viewed from the inside diameter side (inside diameter direction A2). As shown in FIG. 4, the insert unit 56 has a unit main body 58, and a cover body 60. The unit main body 58 is a bottomed tube (a tube with a bottom wall so that the bottom is closed) which has a wide arcuate shape in top plan view and is open at the top, wherein a small chamber (first chamber) 94 on the inside diameter side and a large chamber (second chamber) 95 on the outside diameter side are partitioned from each other by an arcuate wall 93. The small chamber 94 is opening not only at the top but also on the inside diameter side. At an upper portion on the inside diameter side of the small chamber 94, there is provided the tube holder 80 which is plate-shaped and projects to the inside diameter side.

The tube holder 80 has a first guide path 82 for guiding the first tube 18, a second guide path 84 for guiding the second tube 20, and two pins 83 provided at an end portion in the outside diameter direction A1. Each of the first guide path 82 and the second guide path 84 has a groove shape formed by providing walls on both side along the whole length thereof and is opening on the upper side.

The first guide path 82 extends in the inside diameter direction A2 from a nearly central part of an end portion in the outside diameter direction A1 of the tube holder 80, is bent to the first circumferential direction B1 at an intermediate part in the radial direction A, and reaches an outer end of the tube holder 80. A first clamp holding part 86 for holding the first clamp 19 is provided at that portion of the first guide path 82 which forms a groove along the circumferential direction B.

The second guide path 84 extends in the inside diameter direction A2 from that part near the center of an end portion in the outside diameter direction A1 of the tube holder 80 and on the second circumferential direction B2 side relative to the first guide path 82, is bent to the second circumferential direction B1 at an intermediate part in the radial direction A, and reaches an outer end of the tube holder 80. A second clamp holding part 88 for holding the second clamp 21 is provided at that portion of the second guide path 84 which forms a groove along the circumferential direction B.

The tube holder 80 further has a first clamp operating part 90 for operating the first clamp 19 into a closed state and an open state, and a second clamp operating part 91 for operating the second clamp 21 into a closed state and an open state.

The cover body 60 is a cover mounted on the unit main body 58 from the outer side, is configured to cover the outer side, the upper side and the lower side of the unit main body 58, and securely holds the blood bag system 10 mounted to the unit main body 58.

Figure 5:
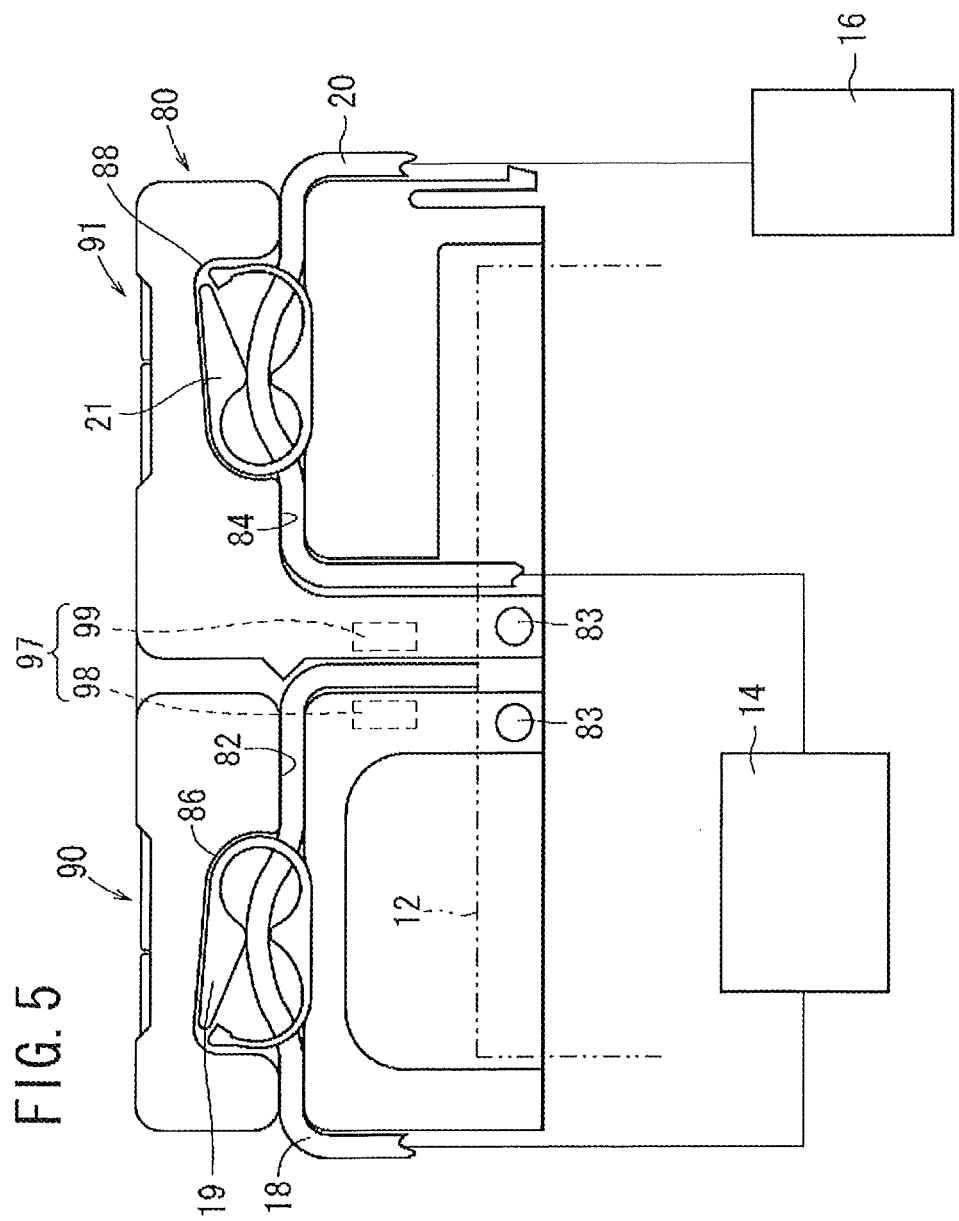
FIG. 5 is a schematic illustration of a condition in which a first tube and a second tube in the blood bag system according to the one embodiment disclosed here by way of example, are held by a tube holder of the centrifuging and transporting apparatus.

FIG. 5 is a schematic illustration of a condition in which the first tube 18 and the second tube 20 are held by the tube holder 80. In addition, in FIG. 5, for easy understanding, a part of the blood collection bag 12 whose upper portion is fixed by the two pins 83 of the tube holder 80 is depicted by imaginary lines; part of the first tube 18 and the second tube 20, the BC bag 14, and the plasma bag 16 are also shown in simplified form, and the other parts of the blood bag system 10 are omitted in the drawing.

As shown in FIG. 5, the blood collection bag 12 is fixed at an upper portion thereof to the tube holder 80 by a method in which the two pins 83, 83 provided on the tube holder 80 are inserted in two holes 12a, 12a (see FIG. 1) provided in the upper portion of the blood collection bag 12. The first tube 18 is mounted and held in the first guide path 82 of the tube holder 80. In addition, the first clamp 19 provided on the first tube 18 is held by the first clamp holding part 86.

The BC bag 14 connected to the other end of the first tube 18 is contained in the large chamber 95 (see FIG. 4). The second tube 20 connected to the outlet of the BC bag 14 is laid around to the tube holder 80, and is mounted and held in the second guide path 84 of the tube holder 80. The second clamp 21 provided on the second tube 20 is held by the second clamp holding part 88.

The plasma bag 16 connected to the other end of the second tube 20 is contained in the large chamber 95 (see FIG. 4). While the third tube 40, the filter 36, the fourth tube 42 and the red cell bag 38 are not specifically illustrated in FIG. 5, they are contained in the large chamber 95. The blood collection tubes 22, 28, the branch tube 30 and the first flow blood bag 32 and the like are cut off after anti-leakage sealing by welding the blood collection tube 22 by a tube sealer or the like, after blood is collected into the blood collection bag 12 and before mounting the blood bag system 10 to the centrifuging and transporting apparatus 50.

As shown in FIG. 5, the tube holder 80 further has a sensor 97 for detecting the kind of liquid passing inside the first tube 18 at a position on the upstream side of the first clamp 19. The sensor 97 includes a light casting part 98 and a light receiving part 99, and the kind of liquid passing these parts can be determined based on the degree of light transmission through the liquid. A plurality of contacts in continuity with the sensor 97 or an interface circuit thereof are provided at a lower surface of the tube holder 80, and these contacts are set in contact with the reception-side electrodes 68 (see FIG. 3) provided on the central body 53a of the centrifugal drum 53, whereby a signal from the sensor 97 can be supplied to the microcomputer.

Figure 6:
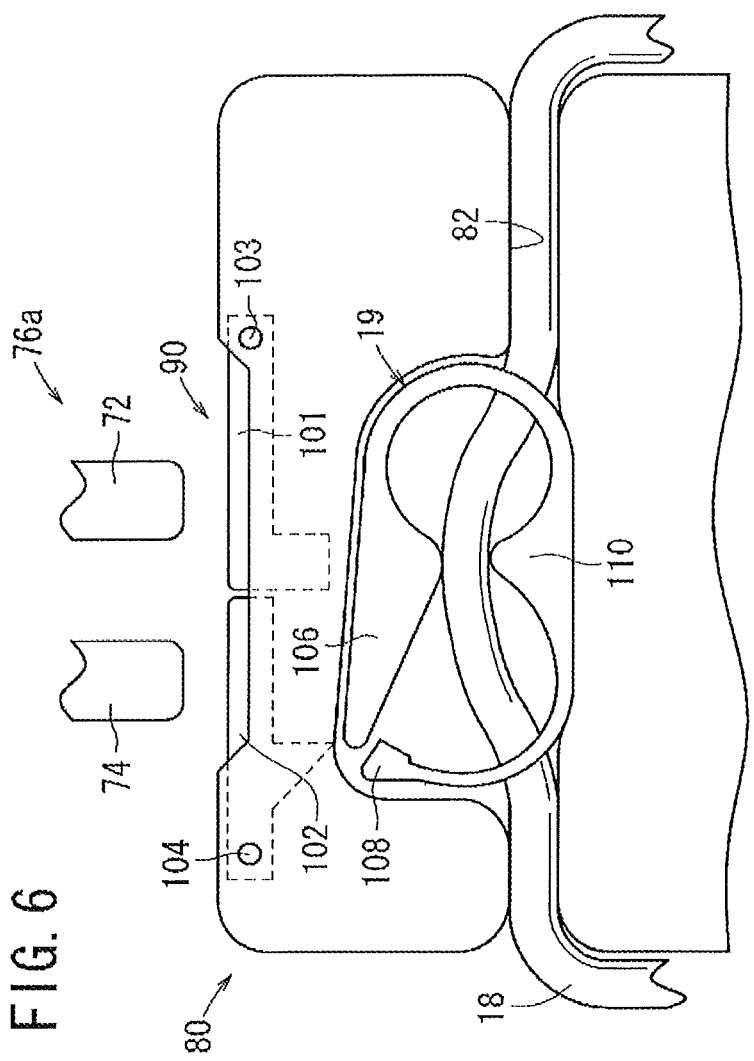
FIG. 6 is a partly omitted enlarged plan view showing a first clamp operating part in the blood bag system according to the one embodiment disclosed here by way of example and the surroundings thereof.

FIG. 6 shows a first clamp operating part 90 and the surroundings of the first clamp operating part 90. As shown in FIG. 6, the first clamp 19 is a resin-made member which has a flattened C-shape as a whole, is provided at its one end with a pressing part 106 for pressing the first tube 18, is provided at its other end with a latch part 108 for engagement with the pressing part 106, is provided with a projected part 110 at a position opposed to the pressing part 106, and is provided at both sides in the longitudinal direction with holes in which the first tube 18 is inserted (through which the first tube 18 passes). The second clamp 21 and the other clamps also have the same structure as the first clamp 19.

With the pressing part 106 pushed into the inner side, the first tube 18 is pinched by an inside projection of the pressing part 106 and the projected part 110, whereby the channel in the first tube 18 can be closed, and the pressing part 106 is held in the state of being engaged with the latch part 108. When the latch part 108 is displaced toward the outer side starting from the condition where the pressing part 106 is held by the latch part 108, the latch part 108 and the pressing part 106 are disengaged from each other and the pressing part 106 is displaced toward the outer side, whereby the channel in the first tube 18 is opened.

As shown in FIG. 6, the first clamp operating part 90 has a first pressing body 101 which is swung by operation of the first rod 72 so as to push in the pressing part 106, and a second pressing part 102 which is swung by operation of the second rod 74 so as to tilt the latch part 108. The first pressing body 101 and the second pressing body 102 are rotatably supported on the tube holder 80 through shaft parts 103, 104, respectively, and are biased in a direction away from the pressing part 106 and the latch part 108 by springs; in addition, they are so configured as to be displaced toward the side of the pressing part 106 and the latch part 108 against biasing forces of the springs when pressed by the first rod 72 and the second rod 74, respectively.

In the first clamp operating part 90 configured as above, with the first rod 72 and the second rod 74 driven to be advanced and retracted, the pressing part 106 and the latch part 108 of the first clamp 19 can be operated, whereby the channel in the first tube 18 can be closed and opened. The second clamp operating part 91 is symmetrical in shape with the first clamp operating part 90.

The blood bag system 10 according to the present embodiment is basically configured as above-described, and its operation and effect will be described below.

Reference is first made to FIG. 1. At the time of collecting blood from a donor, first, the collected blood first flow is sampled into the first flow blood bag 32, as mentioned above. After sampling of the collected blood first flow is completed, the branch tube 30 is closed by the clamp 31, and the above-mentioned breaking operation is applied to the sealing member 24, to put the channel in the blood collection tube 22 into an open state. In this instance, the clamp 23 is set in an open state, whereas the sealing member 17 is set in the initial state (closed state). As a result, the blood from the donor flows into the blood collection bag 12 by way of the blood collection tubes 28, 22. When a predetermined amount of the blood is collected and stored into the blood collection bag 12, the blood collection tube 22 is closed by the clamp 23 so that the blood (whole blood) in the blood collection bag 12 will not flow out. Then, as described above, the blood collection tube 22 is welded and sealed by the tube sealer or the like, followed by cutting off the blood collection tube 22 at the sealed portion.

Next, in order to separate the whole blood collected into the blood bag system 10 into plasma, buffy coat and concentrated red cells and store them respectively in predetermined bags, the blood bag system 10 is mounted to the centrifuging and transporting apparatus 50. At the time of the mounting, first, the channels in the first tube 18 and the second tube 20 are put into a closed state by the first clamp 19 and the second clamp 21, and thereafter the above-mentioned breaking operation is applied to the sealing member 17, to set the channel therein in an open state.

Then, as shown in FIG. 5, the first tube 18 and the second tube 20 are held on the tube holder 80, and the blood collection bag 12 is contained into the small chamber 94 (see FIG. 4) of the unit main body 58, with its upper portion fixed on the tube holder 80. The part ranging from the BC bag 14, the plasma bag 16 and the third tube 40 to the red cell bag 38 is contained into the large chamber 95 (see FIG. 4) of the unit main body 58. In this case, it is recommendable to contain the BC bag 14 and the plasma bag 16 in the large chamber 95 in a non-bent state (see FIG. 7) so that in the separation step after the centrifugation step, the buffy coat and the plasma smoothly flow respectively into the BC bag 14 and the plasma bag 16, to be stored there. As for the filter 36 and the red cell bag 38, they are not used in the centrifugation step and the subsequent separation step; therefore, it is recommendable to contain them in the large chamber 95 after making them compact by, for example, rounding or bending, whereby a space in which to contain the BC bag 14 and the plasma bag 16 can be secured. After the blood bag system 10 is mounted to and contained in the unit main body 58, the cover body 60 is mounted to the unit main body 58, thereby putting the insert unit 56 into an assembled state.

Subsequently, as shown in FIG. 2, the insert unit 56 each with the blood bag system 10 contained therein are inserted into the unit insertion hole 54 in the centrifuging and transporting apparatus 50. As a result, end portions of the tube holders 80 are fixed by the holding levers 67. In addition, the contacts of the sensors or the interface circuits therefor are set in contact with the electrodes 68 (see FIG. 3). Basically, six insert units 56 are mounted to the centrifuging and transporting apparatus 50. However, not more than five insert units 6 (preferably, three or two insert units at regular angular intervals) may be mounted, insofar as they are well-balanced.

Next, the cover 52 of the centrifuging and transporting apparatus 50 is closed, and thereafter the console section 62 is operated, whereby the centrifugation step and the separation step are performed automatically.

In the automatic operation of the centrifuging and transporting apparatus 50, first, the centrifugal drum 53 is rotated to perform the centrifugation step. In this instance, the first clamp 19 and the second clamp 21 are preliminarily closed. For attaining further certainty, however, the first rod 72 is once extended and the first clamp 19 is put into a closed state by the pressing part 106. The second clamp 21 is also set into a closed state.

Figure 7:
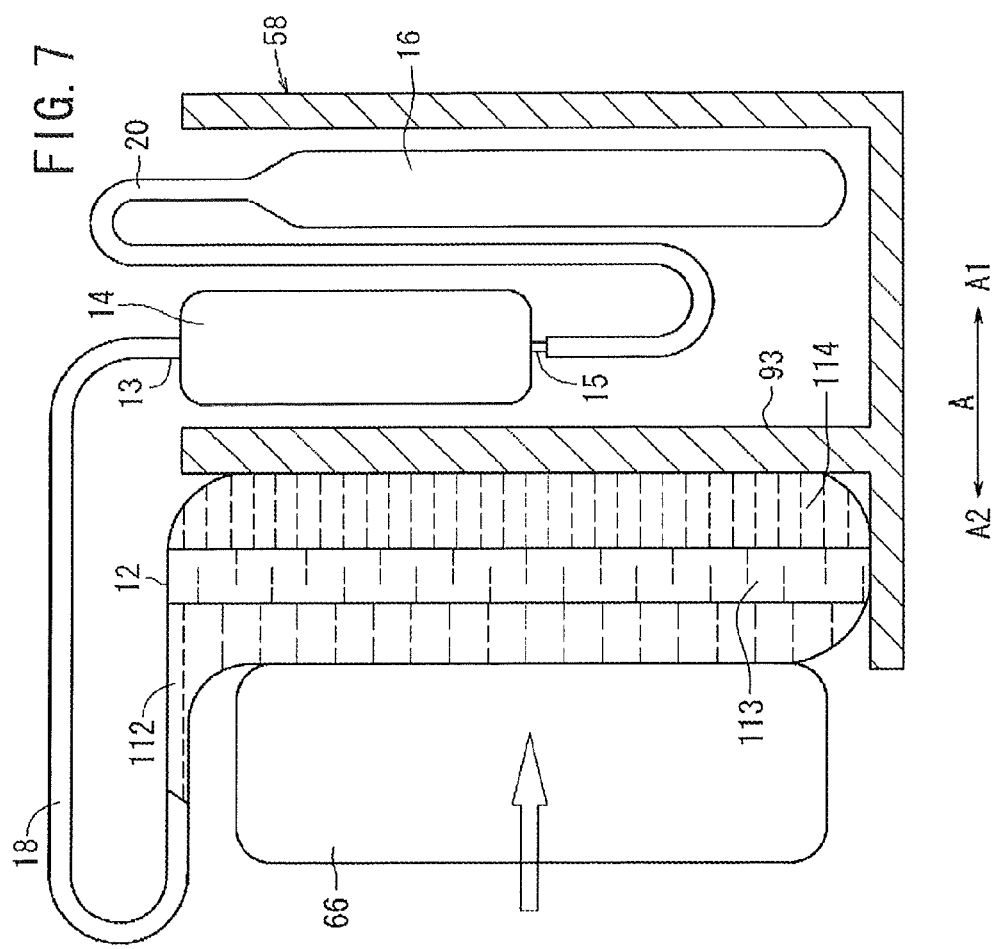
FIG. 7 is an illustration of operation of the centrifuging and transporting apparatus.

In the centrifugation step, as shown in FIG. 7, a centrifugal force is exerted on the whole blood stored in the blood collection bag 12 inside the small chamber 94, whereby concentrated red cell 114 as a high-density component is transferred to the outside diameter direction, plasma 112 as a low-density component is transferred to the inside diameter direction, and buffy coat 113 as a medium-density component is moved to an intermediate region; thus, the whole blood is separated into three layers.

The centrifuging and transporting apparatus 50 starts the separation step after the centrifugation step. In the separation step, while keeping the rotation of the centrifugal drum 53, the first clamp driving means 76a and the second clamp driving means 76b are operated to put the channels in the first tube 18 and the second tube 20 into an open state.

Subsequently, as shown in FIG. 7, the pusher 66 is displaced in the centrifugal direction A1 to press the blood collection bag 12. The blood collection bag 12 is reduced in volume by being clamped between the pusher 66 and a wall, so that the liquid contained therein is discharged via the first tube 18. In this instance, since the first tube 18 is oriented to the inside diameter side, the plasma 112 located most on the inside diameter side flows out of the blood collection bag 12, and flows through the first tube 18, the BC bag 14 and the second tube 20 into the plasma bag 16.

After flowing of the plasma 112 out of the blood collection bag 12 is finished, the buffy coat 113 next starts flowing out of the blood collection bag 12. In this instance, when the flow of the red cells (the red cells contained in the buffy coat) in the first tube 18 is detected by the sensor 97 (see FIG. 5), the channel in the second tube 20 is closed by the second clamp 21, whereby the buffy coat 113 is inhibited from flowing into the plasma bag 16. The flow of the red cells in the first tube 18 can be confirmed by the sensor 97, based on the transparency (in other words, the turbidity) of the liquid flowing in the first tube 18.

As shown in FIG. 7, the BC bag 14 has a structure wherein the cross-sectional area of a channel at the outlet 15 is set to be smaller than the cross-sectional area of a channel at the inlet 13. This setting produces a flow rate difference which helps ensure that a liquid accumulation of a certain amount of the plasma 112 is formed in the BC bag 14, whereby the rate of flow of liquid into the plasma bag 16 can be restrained from becoming excessively high. Therefore, although a certain time lag exists after detection of the red cells by the sensor 97 until the closing of the second tube 20 by the second clamp 21, it is possible, by suppressing the flowing-in rate into the plasma bag 16 through the provision of the flow rate difference as above-mentioned, to securely inhibit or prevent the buffy coat 113 from flowing into the plasma bag 16. The structure of the BC bag 14 in which the cross-sectional area at the outlet 15 is set smaller than the cross-sectional area at the inlet 13 may be replaced by a structure in which the cross-sectional area of the channel in the second tube 20 is set smaller than the cross-sectional area of the channel in the first tube 18, over the whole length of or at a part of the second tube 20.

When the pusher 66 is further advanced and the blood collection bag 12 is pressed by a predetermined amount (a predetermined amount of the buffy coat in the BC bag 14 is collected), the pusher 66 is stopped, and the first clamp driving means 76a is operated to close the channel in the first tube 18 by the first clamp 19.

When the separation step as above is finished, the blood bag system 10 is taken out of the insert unit 56. Further, the first tube 18 and the second tube 20 in the blood bag system 10 are welded and sealed, followed by cutting, whereby each of the bags is cut off.

As above-described, according to the blood bag system 10 in the present embodiment disclosed as an example, a centrifugal force is exerted on the whole blood contained in the blood collection bag 12 to separate the whole blood into the three layers of the plasma 112, the buffy coat 113 and the concentrated red cells 114. Then, the blood collection bag 12 is pressed in the thickness direction thereof, whereby the plasma and the buffy coat are transported from the blood collection bag 12 to the BC bag 14 through the first tube 18, and the plasma 112 is transported from the second bag 14 to the plasma bag 16 through the second tube 20. This helps ensure that, of the blood components centrifugally separated, the buffy coat is stored in the BC bag 14, whereas the plasma 112 is stored in the plasma bag 16, and the concentrated red cells 114 as a residue are left stored in the blood collection bag 12. Consequently, the whole blood is separated into the plasma 112, the buffy coat 113 and the concentrated red cells 114, which are separated (collected) into the respective bags.

In the blood bag system 10 disclosed here, the first tube 18 for transporting the plasma 112 and the buffy coat 113 from the blood collection bag 12 to the BC bag 14 and the plasma bag 16 is connected to an upper portion of the blood collection bag 12. Therefore, a tube to be connected to a lower portion of the blood collection bag 12 is unnecessary, and the tubes are connected only to the upper portion of the blood collection bag 12 in this configuration. Accordingly, the bag configuration is simplified, so that the convenience for the user in using the blood bag system 10 is enhanced. In addition, handling of the tubes in mounting the blood bag system 10 to the centrifuging and transporting apparatus 50 is facilitated, so that the mounting to the centrifuging and transporting apparatus 50 is facilitated.

As for the concentrated red cells 114 left in the blood collection bag 12, leukocytes can be removed therefrom through filtration by the filter 36, and the concentrated red cells 114 freed of the leukocytes can be stored in the red cell bag 38. In addition, since the third tube 40 through which the blood collection bag 12 and the filter 36 are connected is connected to an upper portion of the blood collection bag 12, a tube to be connected to a lower portion of the blood collection bag 12 is unnecessary. Thus, the blood collection bag 12 has a top-and-top (TAT) type bag structure in which the tubes are connected only to the upper portion of the bag. Consequently, in spite of the configuration in which the filter 36 is provided, handling of the tubes at the time of mounting the blood bag system 10 to the centrifuging and transporting apparatus 50 is relatively easy to perform, so that the mounting to the centrifuging and transporting apparatus 50 is easy to carry out.

The BC bag 14 is used only for storing the buffy coat, and its capacity may be set according to the amount of the buffy coat to be stored therein. This permits a reduction in size of the BC bag 14, as compared with a conventional buffy coat bag. Consequently, the amount of the buffy coat left in the BC bag 14 at the time of preparing a platelet preparation by the buffy coat pooling conducted as the subsequent step can be reduced, and the platelet recovery rate can be thereby enhanced.

Figure 8:
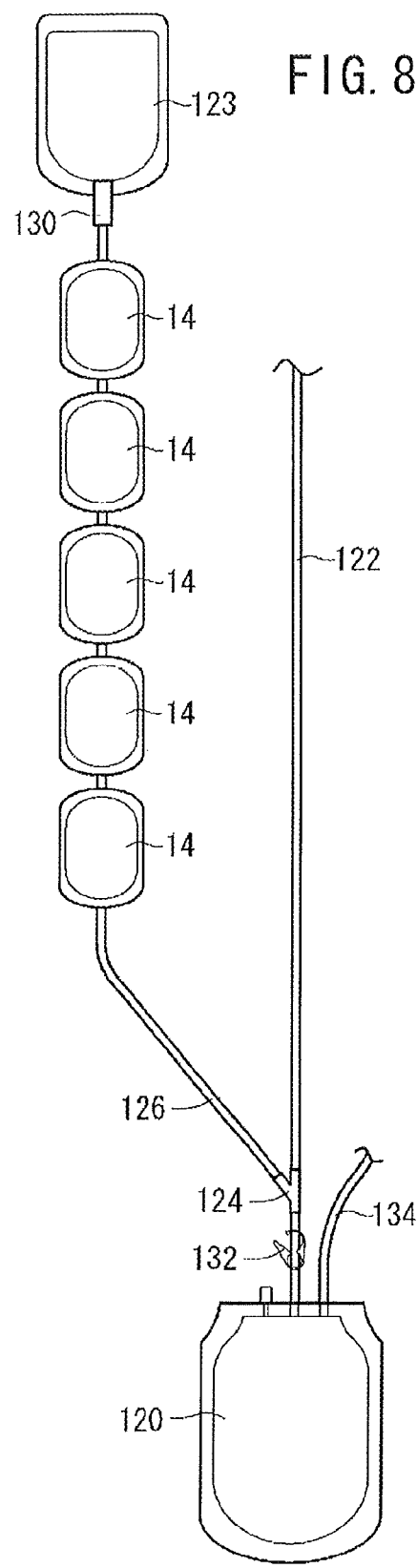
FIG. 8 is an illustration of buffy coat pooling.

Now, description will be made of "buffy coat pooling" (hereinafter referred to as BC pooling) which is a treatment wherein the contents of a plurality of BC bags 14 containing the buffy coat obtained by the above-mentioned treatment are transported and collected into a single bag. As shown in FIG. 8, in the BC pooling, a plurality of the BC bags 14 are connected in series, by use of respective tube joining devices, to a tube 126 connected to a BC pooling bag 120. In the BC bags 14, the buffy coat obtained by the above-mentioned treatment is contained. In addition, a clamp 132 is in a closed state.

Next, to a tube of the BC bag 14 at a terminal end, a storage solution bag 123 containing a platelet storage solution is connected by use of a tube joining device. Thereafter, the storage solution bag 123 is hung from a hanger (not shown), and the clamp 132 is opened to open a channel between a branch connector 124 and the BC pooling bag 120, whereby the buffy coat is collected from the BC bags 14 into the BC pooling bag 120. In this instance, platelets are left adhering to inside walls of the BC bags 14. Therefore, the buffy coat in the BC bags 14 is washed away in the following manner.

A breaking operation is applied to a sealing member 130 of the storage solution bag 123 to open a channel, whereby the platelet storage solution is transported into the BC bags 14, and the buffy coat remaining in the BC bags 14 is mixed with the platelet storage solution and moved into the BC pooling bag 120. Thereafter, a tube 122 is welded at a part near the BC pooling bag 120 by use of a tube sealer or the like, to be thereby sealed in a leak-free manner, and is cut.

Here, in the BC pooling as above-mentioned, the BC bags 14 can be connected in parallel with each other. In that case, the BC bags 14 are connected respectively to a plurality of tubes branched from the tube 126, and the storage solution bags 123 are connected to the tubes 122 branched from the tube 126 by branch connectors 124, whereby BC pooling is conducted. In the case where the BC bags 14 are connected in series with each other as shown in FIG. 8, however, the platelet storage solution is moved sequentially into the plurality of BC bags 14, so that the platelets adhering inside the BC bags 14 can be effectively washed away by a simple operation. Therefore, buffy coat recover rate is enhanced, with the result that the recovery rate of the platelets obtained by centrifugation of the buffy coat can be enhanced.

In addition, while the plurality of BC bags 14 must each be provided with ports at an upper portion and a lower portion thereof in order to be connected in series with each other, the BC bag 14 in the blood bag system 10 according to the present invention is convenient for adoption of a series connection mode in BC pooling, since the BC bag 14 has a top-and-bottom (TAB) type bag structure wherein it is provided with the inlet 13 and the outlet 15 as above-mentioned.

To the BC pooling bag 120 is connected another tube 134, and to a terminal end of this tube 134 are sequentially connected a leukocyte removal filter and a platelet storage bag. After the BC pooling, the buffy coat in the BC pooling bag 120 is centrifugally separated into a supernatant liquid and a precipitated liquid, and the supernatant liquid thus obtained is transported to the platelet storage bag through the above-mentioned leukocyte removal filter. The centrifugation step and the separation step in this case may be carried out by use of the above-mentioned centrifuging and transporting apparatus 50.

While a treatment for centrifuging whole blood into three components of plasma, buffy coat and concentrated red cells has been described in the present embodiment, the present invention is not limited to this. For example, the invention may be applied to a treatment in which blood obtained by preliminarily removing leukocytes is centrifugally separated into three components including a low-density component, a medium-density component and a high-density component, that is, three components including plasma (leukocyte-freed plasma), concentrated platelets (leukocyte-freed concentrated platelets) and concentrated red cells (leukocyte-freed concentrated red cells).

The detailed description above describes a blood bag system and blood treatment method. The inventions here are not limited, however, to the precise embodiments and variations described above and illustrated in the drawing figures. Various changes, modifications and equivalents could be effected by one skilled in the art without departing from the spirit and scope of the invention as defined in the appended claims. It is expressly intended that all such changes, modifications and equivalents which fall within the scope of the claims are embraced by the claims.

What is claimed is:

1. A blood treatment method comprising:
   centrifuging blood containing a plurality of components and located in a first bag to separate the blood into a relative low-density component, a relative medium-density component and a relative high-density component in the first bag;
   transporting the relative low-density component from the first bag to a third bag through a first tube which opens into an upper portion of the first bag by pressing the first bag;
   transporting the relative medium-density component from the first bag to a second bag provided fluidly between the first bag and the third bag through the first tube by pressing the first bag;
   after the transporting of the relative low-density component to the third bag and after the transporting of the relative medium-density component to the second bag, transporting the relative high-density component remaining in the first bag from the first bag to a filter by which predetermined cells are removed from the relative high-density component, the relative high-density component being transported from the first bag to the filter by way of a third tube connected to the filter and to an upper portion of the first bag;
   transporting the relative high-density component which has passed through the filter from the filter to a fourth bag; and
   the flow of the high-density component from the first bag through the filter is the first flow through the filter.

2. The blood treatment method according to claim 1, wherein:
   the pressing of the first bag to transport the relative low-density component and the relative medium-density component causes the relative low-density component to first flow out of the first bag through the first tube while the relative medium-density component remains in the first bag;
   the relative low-density component is transported to the third bag by first passing through the first tube, next passing through the second bag and then next passing through a second tube connected to an outlet of the second bag; and
   the relative medium-density component is transported to the second bag through the first tube only after the relative low-density component has been transported to the second bag.

3. The blood treatment method according to claim 2, further comprising detecting, during the transporting of the relative low-density component and the medium-density component through the first tube from the first bag to the second bag, whether the component in the first tube is the relative low-density component or the relative medium-density component, and closing the second tube when it is detected that the component in the first tube is the relative medium-density component.

4. The blood treatment method according to claim 1, further comprising closing the first tube to stop the transport of the relative low-density component and the relative medium-density component when the first bag has been pressed by a predetermined amount.

5. The blood treatment method according to claim 1, wherein the blood containing the plurality of components is whole blood, and the relative low-density component, the relative medium-density component and the relative high-density component are plasma, buffy coat and concentrated red cells, respectively.

6. A blood treatment method comprising:

centrifuging blood containing a plurality of components and located in a first bag to separate the blood into a relative low-density component, a relative medium-density component and a relative high-density component in the first bag, the first bag being disposed between a pusher and a wall in a centrifuge;

the centrifuging being performed so that the relative low-density component, the relative medium-density component and the relative high-density component are positioned horizontally side-by-side in the first bag;

transporting the relative low-density component from the first bag to a third bag through a first tube which opens into an upper portion of the first bag by pressing the first bag against the wall with the pusher;

after transporting the relative low-density component to the third bag, transporting the relative medium-density component from the first bag through the first tube and to a second bag by further pressing the first bag against the wall with the pusher, the second bag being positioned fluidly between the first bag and the third bag;

after transporting of the relative medium-density component to the second bag, transporting the relative high-density component remaining in the first bag from the first bag to a filter by which predetermined cells are removed from the relative high-density component, the relative high-density component being transported from the first bag to the filter by way of a third tube connected to the filter and to an upper portion of the first bag;

transporting the relative high-density component which has passed through the filter from the filter to a fourth bag; and the flow of the high-density component from the first bag through the filter is the first flow through the filter.

7. The blood treatment method of claim 6, wherein the relative low-density component is transported to the third bag by first passing through the first tube, next passing through the second bag and then next passing through a second tube connected to an outlet of the second bag, the first tube being connected to an inlet of the second bag, and a cross-sectional area of an interior of the second bag at the outlet is smaller than a cross-sectional area of the interior of the second bag at the inlet.

8. The blood treatment method of claim 6, wherein the relative low-density component is transported to the third bag by first passing through the first tube, next passing through the second bag and then next passing through a second tube connected to an outlet of the second bag, and a cross-sectional area of a lumen of the second tube is smaller than a cross-sectional area of a lumen of the first tube.

* * * * *